United States Patent
Harraz et al.

(10) Patent No.: US 10,809,220 B1
(45) Date of Patent: Oct. 20, 2020

(54) METHOD FOR CHEMICAL SENSING AND PHOTOCATALYSIS WITH SILVER NANOPARTICLES/MESOPOROUS SILICON NANOCOMPOSITE

(71) Applicant: NAJRAN UNIVERSITY, Najran (SA)

(72) Inventors: Farid A Harraz, Najran (SA); Mohd Faisal, Najran (SA); Mohammad S Al-Assiri, Najran (SA); Ahmed Mohamed El-Toni, Riyadh (SA)

(73) Assignee: Najran University, Najran (SA)

( * ) Notice: Subject to any disclaimer, the term of this patent is extended or adjusted under 35 U.S.C. 154(b) by 4 days.

(21) Appl. No.: 16/507,519

(22) Filed: Jul. 10, 2019

(51) Int. Cl.
*G01N 27/30* (2006.01)
*B01J 23/50* (2006.01)
*B01J 35/10* (2006.01)
*B01J 21/06* (2006.01)
*B01J 35/00* (2006.01)
*B01J 19/12* (2006.01)
*G01N 33/00* (2006.01)

(52) U.S. Cl.
CPC .......... *G01N 27/305* (2013.01); *B01J 19/127* (2013.01); *B01J 21/06* (2013.01); *B01J 23/50* (2013.01); *B01J 35/004* (2013.01); *B01J 35/0013* (2013.01); *B01J 35/1061* (2013.01); *G01N 33/0047* (2013.01)

(58) Field of Classification Search
CPC ............... G01N 27/305; G01N 27/308; G01N 33/0047; B01J 19/127; B01J 21/06; B01J 23/50; B01J 35/0013; B01J 35/002; B01J 35/004; B01J 35/0046; B01J 35/0066; B01J 35/1052; B01J 35/1061; B05D 5/12
See application file for complete search history.

(56) References Cited

U.S. PATENT DOCUMENTS

| | | | | |
|---|---|---|---|---|
| 6,906,208 B2 * | 6/2005 | Shan | ........................ | B01J 21/06 549/525 |
| 2014/0021967 A1 * | 1/2014 | Kang | ................. | G01N 33/0047 324/679 |
| 2014/0251786 A1 * | 9/2014 | Landry | .................. | B01J 19/127 204/157.15 |

OTHER PUBLICATIONS

Kaur et al., Simultaneous and sensitive determination of ascorbic acid, dopamine, uric acid, and tryptophan with silver nanoparticles-decorated reduced graphene oxide modified electrode, Colloids and Surfaces B: Biointerfaces, vol. 111, pp. 97-106 (2013) (Year: 2013).*

(Continued)

*Primary Examiner* — Maris R Kessel
*Assistant Examiner* — Vivian A Tran
(74) *Attorney, Agent, or Firm* — Geeta Kadambi; Riddhi IP LLC

(57) ABSTRACT

The synthesis of silver nanoparticles (AgNPs)/meso-porous silicon (PSi) nanocomposite and its effective use as efficient chemical sensor and photocatalyst are described. The PSi was prepared via a simple stain etching of Si microparticles in $HF/HNO_3$ aqueous solution, followed by the deposition of AgNPs onto stain etched PSi by the immersion plating technique. The resultant nanocomposite is used successfully for (i) enhanced electro-oxidation and quantification of ascorbic acid (AA) on modified glassy carbon electrode and (ii) for the photo-reduction of hexavalent chromium Cr(VI) to trivalent Cr(III) under direct visible light irradiation in the presence of citric acid.

4 Claims, 14 Drawing Sheets

(56) References Cited

OTHER PUBLICATIONS

Gupta et al., Gold nanoparticles impregnated mesoporous silica spheres for simultaneous and selective determination of uric acid and ascorbic acid, Sensor and Actuators B: Chemical, vol. 219, pp. 139-145 (2015) (Year: 2015).*

Rahman et al., CuO Codoped ZnO Based Nanostructured Materials for Sensitive Chemical Sensor Applications, ACS Applied Materials & Interfaces, vol. 3, No. 4, pp. 1346-1351 (2011) (Year: 2011).*

Zhao et al., Formation of silver single crystal polyhedra with high catalytic activity toward oxidation of ascorbic acid in highly ordered SiO2 cavities, Journal of Electroanalytical Chemistry, vol. 768, pp. 41-46 (2016) (Year: 2016).*

Tiğ, Development of electrochemical sensor for detection of ascorbic acid, dopamine, uric acid and l-tryptophan based on Ag nanoparticles and poly(l-arginine)-graphene oxide composite, Journal of Electroanalytical Chemistry, vol. 807, pp. 19-28 (2017) (Year: 2017).*

Harraz, Porous silicon chemical sensors and biosensors: A review, Sensors and Actuators B: Chemical, vol. 202, pp. 897-912 (2014) (Year: 2014).*

Harraz et al., Surface-enhanced Raman scattering (SERS)-active substrates from silver plated-porous silicon for detection of crystal violet, Applied Surface Science, vol. 331, pp. 241-247 (2015) (Year: 2015).*

Rahman et al., Development of selective and sensitive bicarbonate chemical sensor based on wet-chemically prepared CuO-ZnO nanorods, Sensors and Actuators B: Chemical, vol. 214, pp. 82-91 (2015) (Year: 2015).*

Rahman et al., Electrochemical determination of olmesartan medoxomil using hydrothermally prepared nanoparticles composed SnO2—Co3O4 nanocubes in tablet dosage forms, Talanta, vol. 99, pp. 924-931 (2012) (Year: 2012).*

Noroozifar et al., Preparation of silver hexacyanoferrate nanoparticles and its application for the simultaneous determination of ascorbic acid, dopamine and uric acid, Talanta, vol. 80, Issue 5, pp. 1657-1664 (2010) (Year: 2010).*

Qiu et al., Electrochemical impedance spectroscopy sensor for ascorbic acid based on copper(I) catalyzed click chemistry, Biosensors and Bioelectronics, vol. 26, Issue 11, pp. 4326-4330 (2011) (Year: 2011).*

Ensafi et al., Electrochemical sensor based on porous silicon/silver nanocomposite for the determination of hydrogen peroxide, Sensors and Actuators B: Chemical, vol. 231, pp. 239-244 (2016) (Year: 2016).*

* cited by examiner

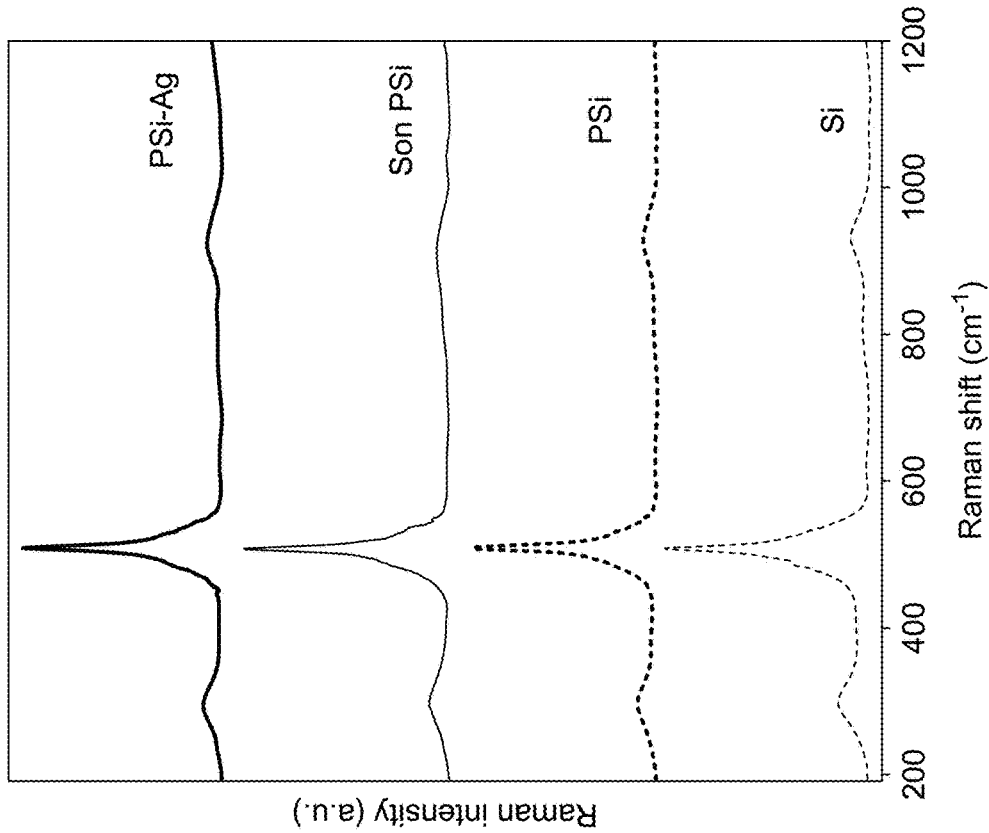
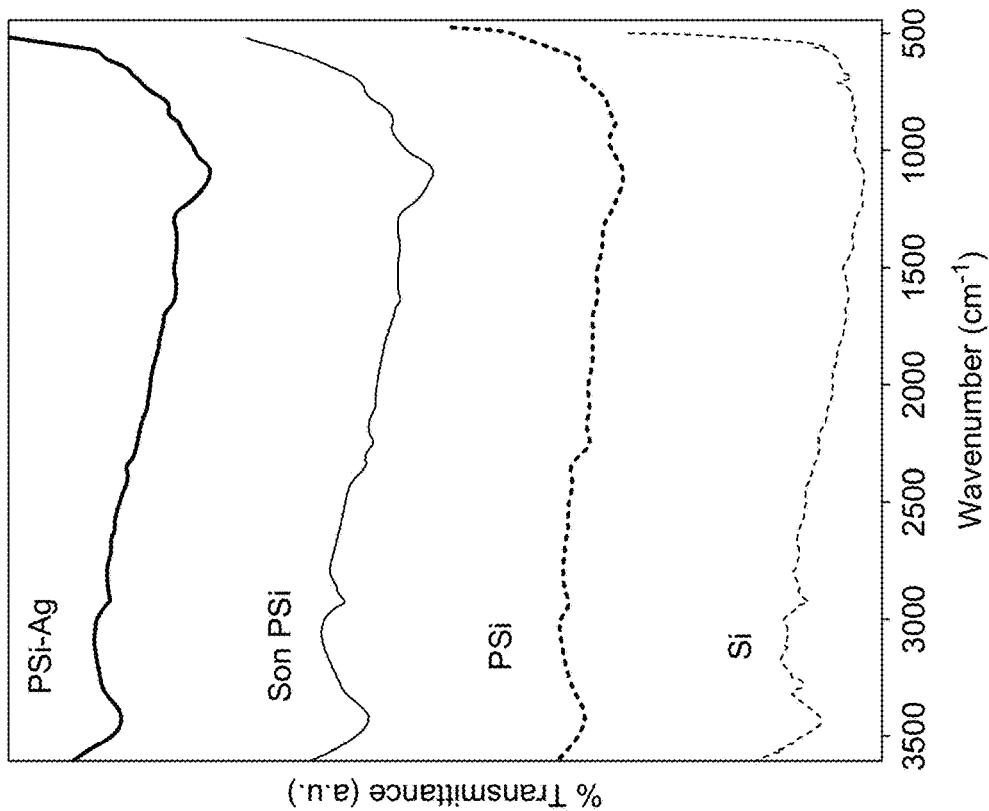
FIG. 2A
FIG. 2B

METHOD FOR CHEMICAL SENSING AND PHOTOCATALYSIS WITH SILVER NANOPARTICLES/MESOPOROUS SILICON NANOCOMPOSITE

FIELD OF TECHNOLOGY

The current disclosure describes a method of making a nanocomposite made of meso-porous silicon (PSi) nanopowder deposited with silver nanoparticles (AgNPs) and to be used as efficient chemical sensor and photocatalyst.

BACKGROUND

Porous silicon (PSi) is generally fabricated by electrochemical anodization of Si in hydrofluoric acid-based solutions and the produced porous films could offer many advantages for chemical and biosensing applications (M. Ruminski et. al. 2010, F. A. Harriz 2014). The rationale of using PSi in sensors is basically related to its huge surface area with open, reactive porous structures, electrical-optical characteristics and controllable surface modification and functionalization (F. A. Harriz et. al. 2015). However, the standard anodization procedure is not appropriate to produce PSi nanopowder, characterized by much larger porosity-to-weight ratio, hence there is need to further modify the working electrodes for various sensor-related fields (A. A. Ensafi et. al. 2017).

Ascorbic acid (AA) is widely used in various food-drinks related industries and essentially plays indispensable role in humans' physiological processes. The development of rapid, sensitive approach for accurate detection of AA is therefore of considerable importance. Among several sensing methods, the electrochemical technique is highly nominated owing to simplicity in operation, sensitivity and rapid response. However, the effective sensing of AA at suboptimal working electrodes are often hindered by highly-induced overpotential and electrode fouling effect (G. P. Keeley et. al. 2010). There is a need to mitigate these drawbacks and provide a more sensitive and effective sensing electrode for AA determination and quantification.

Chromium in its hexavalent form i.e. Cr(VI) is one of the most common hazardous pollutants. It is a strong oxidant and considered highly toxic in nature. Wide range of utilization of Cr(VI) in various sectors such as electroplating, tanning, stainless steel, dyes, leather, wood preservatives, ceramic glazes, refractory bricks and many others ultimately led to contamination of soil and ground water creating an alarming situation for monitoring agencies and scientific communities. Chromium occurs in nature in several diverse forms of which Cr metal and Cr(III) ions are safe but Cr(VI) is notably hazardous and carcinogenic (H. Oliveira 2012). So, it is highly desirable and urgently required to remove such Cr(VI) ions from the environment by conversion or reduction to the Cr(III) form.

The photocatalytic approach for the treatment of harmful, toxic pollutants in air or water attracted much attention and proven to be highly efficient for the treatment of hazardous compounds. So, the reduction of Cr(VI) to Cr(III) in the presence of efficient photocatalyst will be easier and proper technique to achieve such conversion process. Several reports are well documented in the literature about semiconductor mediated photocatalytic reduction of Cr(VI) to Cr(III). For instance, Wang and coworker successfully utilized organic acid modified $TiO_2$ under visible light for the reduction of Cr(VI) (N. Wang et. al. 2010). Ku et al. (2011) applied coupled $NiO/TiO_2$ structures for the photocatalytic reduction of Cr(VI) in aqueous solution. Photocatalytic reduction of Cr(VI) under laser light in the presence of NiO nanostructures has been accomplished by Qamar and his group (2011). Zhang et al. (2012) synthesized highly active $SnS_2/TiO_2$ nanocomposites for the reduction of Cr(VI) under visible light. Yang et. al. (2010) utilized $WO_3$ doped $TiO_2$ nanotubes in the presence of citric acid for the photocatalytic reduction of Cr(VI). There is a need for making a nanocomposite that would address the need for such a reduction-conversion process with efficient photocatalytic activity.

SUMMARY

The instant disclosure and invention describes a novel nanocomposite fabrication that has several uses. In one embodiment, silver nanoparticles (AgNPs) modified PSi is disclosed. In one embodiment, a meso-porous silicon (PSi) nanopowder deposited with silver nanoparticles (AgNPs) is disclosed. In one embodiment, meso porous silicon was made via simple stain etching of Silicon (Si) microparticles in $HF/HNO_3$ aqueous solution to produce PSi nanopowder is disclosed. In another embodiment, the deposition of silver nanoparticles (AgNPs) onto PSi nanopowder by the immersion plating technique is disclosed. In another embodiment, a novel ascorbic acid (AA) amperometric sensor was developed based on glassy carbon electrode (GCE) modified with AgNPs/PSi nanocomposite.

In another embodiment, due to enhanced electrooxidation reaction of AA, the current modified electrode exhibited high sensitivity, selectivity, rapid response with acceptable detection result toward a commercial vitamin C tablet. In another embodiment, photocatalytic reduction of Cr(VI) to Cr(III) was evaluated using the AgNPs modified PSi nanocomposite in the presence of citric acid under visible light irradiation was disclosed.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

FIG. 2A. FTIR and FIG. 2B Raman spectra of Si microparticles, stain-etched PSi, sonicated PSi and AgNPs modified PSi nanocomposite.

FIG. 9A, 9B, 9C, 9D Changes in the UV-vis absorbance spectra with irradiation time during the photo-reduction of Cr(VI) on: (FIG. 9A) unmodified PSi and (FIG. 9B) AgNPs modified PSi nanocomposite photocatalysts. (FIG. 9C) Temporal ($C_0/C$) concentration changes during the photocatalytic reduction of Cr(VI) in absence of the photocatalyst (blank), unmodified PSi and AgNPs/PSi nanocomposite photocatalysts. K$_2$Cr$_2$O$_7$ concentration: 30 mg/L, loading of photocatalyst: 1 g/L, citric acid: 5 mM. (FIG. 9D) The reusability behavior of AgNPs/PSi nanocomposite photocatalyst during five cyclic runs.

Figure 1:
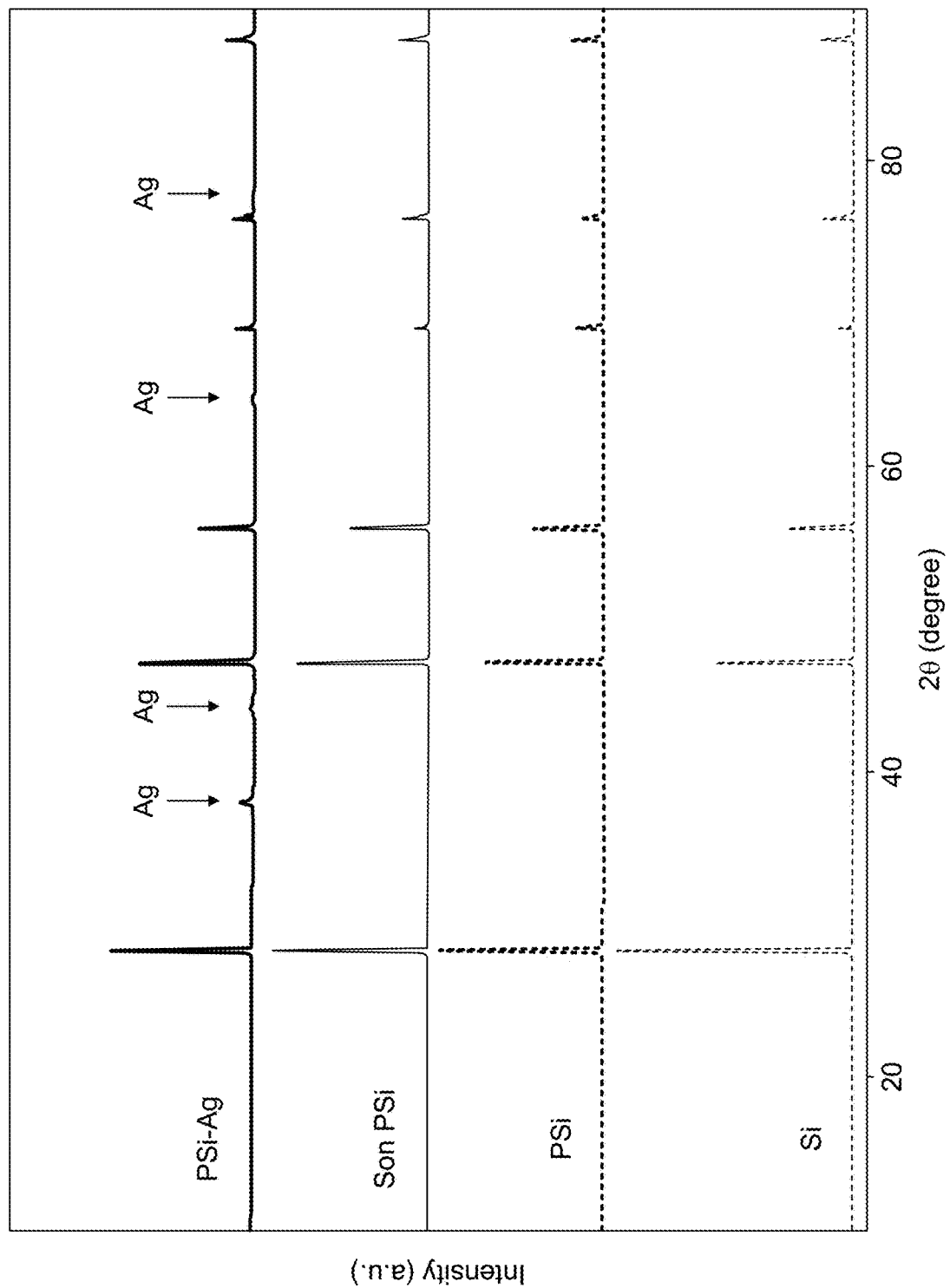
FIG. 1. XRD patterns of initial Si microparticles, stain-etched PSi, sonicated PSi and AgNPs modified PSi.

Other features of the present embodiments will be apparent from the accompanying drawings and from the detailed description that follows.

DETAILED DESCRIPTION

In the present disclosure, chemical sensors and visible-light photocatalysts with desirable material characteristics and efficient performance is an existing challenge for sensors and photocatalysis community. Herein, we report on the synthesis of AgNPs-PSi nanocomposite by deposition of silver nanoparticles (AgNPs) onto meso-porous silicon (PSi) nanopowder and its effective use as efficient chemical sensor and photocatalyst. The PSi was prepared via simple stain etching of Silicon (Si) microparticles in HF/HNO$_3$ aqueous solution, followed by the deposition of AgNPs onto PSi by the immersion plating technique. The newly developed nanocomposite composed of PSi with <20 nm mesoporous structure, decorated with crystalline 15-50 nm AgNPs. The developed nanocomposite was then applied successfully for (i) enhanced electro-oxidation and quantification of ascorbic acid (AA) and (ii) for the photo-reduction of hexavalent chromium Cr(VI) to trivalent Cr(III) under direct visible light irradiation in the presence of citric acid. Remarkable sensing performance toward AA was achieved with high sensitivity (1.279 µAµM$^{-1}$ cm$^{-2}$), fast response time (<5 s), wide linear range (20 to 600 µM: R$^2$=0.9933), low limit of detection (0.83 µM at S/N=3) and excellent anti-interference and repeatability behavior. The current AgNPs-PSi modified glassy carbon electrode was further applied to a commercially available vitamin C supplement with satisfactory detection result. Additionally, the photocatalytic experiments using unmodified Si microparticles, either PSi or sonicated one, indicated inactive catalytic behavior towards the photo-reduction of Cr(VI). Remarkable photo-reduction efficiency (97.4%) was achieved after 180 min irradiation using the AgNPs/PSi sample. The efficient photo-reduction capability of AgNPs/PSi nanocomposite photocatalyst is attributed to the enhanced separation between photo-generated electrons and holes (e$^-$-h$^+$) enabling better utilization of light, as revealed from the photoluminescence measurement. Additionally, the presence of citric acid in solution promoted greatly the photo-reduction reaction as it acted as a hole scavenger, suppressing further the rate of e$^-$-h$^+$ recombination through rapidly consumption of photo-generated holes. Excellent reusability of the current photocatalyst was evidenced by performing cyclic five runs with minimal reactivity loss. Results of synthesis on novel nanocomposite, full characterization, sensing performance, photocatalytic activity and reaction mechanism are thoroughly addressed and discussed. Several investigations have been done to exploit this proficient material silicon in various applications including photovoltaic applications, drug delivery, catalysis, Si-on-insulator, biotechnology, micromachining, sensors and many others. PSi possesses various highly acceptable features like simple and cost effective synthesis technique, large specific surface area, biocompatibility, biodegradability, possibility to modify pore size and morphology by changing various parameters. Even though, the bulk Si possesses narrow band gap energy (~1.1 eV) but it is limited to the heterogeneous photocatalysis as its valence band positivity is not quite enough to oxidize, degrade the target organic pollutants O. Fellahi et. al. 2016).

Recently silicon with nanowires morphology i.e. (SiNWs) has been utilized as photocatalysts for the degradation of dyes and toxic organic pollutants. So far, PSi microparticles with meso-porosity (pores 2-50 nm) has not been exploited so much for the photocatalytic applications. Formation of hybrid structures of noble metals and PSi may improve the spectral features of PSi which can lead to efficient charge transfer through noble metal-PSi interface. Additionally, the hybrid structure of metal nanoparticles, noble, less noble or non-noble with PSi can prevent surface oxidation and impart stability to the framework (F. A. Harraz et. al. 2013). These advantages of hybrid structures prompted us to synthesize PSi nanopowder and modify the porous matrix with AgNPs, then utilize it as a photocatalyst for the photo-reduction of toxic Cr(VI) to nontoxic Cr(III). The choice of AgNPs to modify the PSi matrix is mainly related to their unique physicochemical properties and their frequent utilization in various research and technological applications including food industry, medical and health care as well as in different industrial purposes including photocatalysis related fields. The instant application describes below the method of making, the utilization of PSi—AgNPs hybrid structure as both AA sensor and as a photocatalyst for the reduction of aqueous Cr(VI) under visible light illumination in detail.

Formation of Porous Silicon Nanopowder:

Porous silicon (PSi) nanopowder was synthesized according to our recent report (F. A. Harraz et. al. 2019). Briefly, 1 g Si micro-particles ~40 µm was dispersed in an aqueous mixture composed of: 40 mL distilled water+10 mL 48% HF+2.5 mL 70% HNO$_3$ at room temperature and under continuous stirring. The stain etching of Si precursors to form PSi nanopowder was complete within 15 min, with the appearance of nitrogen oxide vapor. The as-synthesized nanopowder was filtered, washed with pure water and left for drying. In another experiment, a sample of as-formed PSi nanopowder was re-dispersed in water and sonicated for 30 min, the sample called Son PSi. The chemical reaction involved during the stain etching of Si particles in a mixture of HF/HNO$_3$ can be described by the following equation:

$$3Si + 4HNO_3 + 18HF \rightarrow 3H_2SiF_6 + 4NO + 8H_2O \quad \text{Equation 1}$$

Formation of AgNPs modified porous silicon nanopowder: The as-formed PSi nanopowder was subsequently modified with AgNPs using the simple immersion plating method. 0.5 g PSi powder was dispersed in 80 mL from 0.1M hydrofluoric acid (HF). During stirring the above mixture, 5 mL of 0.05M AgNO$_3$ was added dropwise. Under such a situation, PSi could act as a mild reducing agent and thus metallic AgNPs were immediately deposited onto PSi surface via a simple galvanic displacement reaction without the need to any external reducing agent. The as-synthesized AgNPs modified PSi nanopowder was accordingly filtrated, dried and finally collected for use. It is worthy to mention again that the deposition of Ag occurs at the open circuit potential; the redox potential of Ag ions is larger than that of hydrogen (0.779 V) and thus Ag ions could withdraw electrons from Si and readily reduced and deposited onto the surface. The cathodic reaction can be expressed as:

$$Ag^+ + e^- = Ag^0 \quad E^0 = 0.779 \text{ V} \quad \text{Equation 2}$$

As a counter anodic reaction, the Si is oxidized according to the following equation:

$$Si + 2H_2O = SiO_2 + 4H^+ + 4e^- \quad \text{Equation 3}$$

In the presence of HF, the oxide is readily dissolved according to the following reaction:

$$SiO_2 + 6HF = H_2SiF_6 + 2H_2O \quad \text{Equation 4}$$

Materials characterization: X-ray diffraction (XRD) patterns of newly prepared samples have been performed on Bruker AXS D4 Endeavour X diffractometer using Cu K$\alpha_{1/2}$, $\lambda\alpha_1$=154.060 pm, $\lambda\alpha_2$=154.439 pm radiation. Fourier transforms infrared spectrometer (FT-IR; Perkin Elmer) was used to record the FTIR spectra in KBr dispersion at room temperature. Perkin Elmer Raman Station 400 was utilized to obtain Raman spectra for all samples under investigation at room temperature. Field emission-secondary electron microscope (FE-SEM) with a FE scanning electron micro analyzer (JEOL-6300F, 5 kV) attached with energy dispersive spectroscopy (EDS) and Transmission electron microscopy (TEM) performed at 200 kV with a JEOL supplied JEM-2100E-UHR field-emission instrument fitted with a Gatan GIF 2001 energy filter and a 1k-CCD (charge-coupled device) camera in order to obtain EEL (Electron energy loss) spectra was used to examine structure and surface morphology of all samples. UV-Vis optical absorption spectra were measured by spectrophotometer (lambda 950 Perkin Elmer). Room temperature photoluminescence (PL) spectra were also recorded using spectrofluorophotometer, (RF-5301 PC, Japan, SHIMADZU, 400 W, 50/60 Hz) at 450 nm excitation wavelength produced by a 150 W xenon lamp. Nitrogen adsorption/desorption isotherms were obtained by Quantachrome NOVA Station A at 77 K after the samples were vacuum-dried at 300° C. for 3 h. Sorption data were obtained by applying Barrett-Joyner-Halenda (BJH) model with Halsey equation.

Sensor fabrication and electrochemical measurements: Glassy carbon electrode (GCE), was modified by either PSi or AgNPs-PSi nanopowder as active sensing material using a binder (butyl carbitol acetate/ethyl acetate). The active material of either PSi or AgNPs-PSi nanopowder is mixed with the butyl carbitol acetate/ethyl acetate binder with weight % of 80% from active material to 20% binder forming finally an active paste. Such a paste is readily coated into the surface of GCE followed by drying at 65° C. for 6 h until a uniform, dried GCE surface is obtained. A three-electrode configuration was employed using ZahnerZennium electrochemical workstation, (working electrode (WE): modified GCE; counter electrode (CE): Pt wire and reference electrode (RE): Ag/AgCl). Before use, the GCE, (Bio-Logic SAS), with surface area 0.071 cm$^2$, was polished using 1 µm diamond and 0.05 µm alumina slurry and then rinsed in ethanol and distilled water. The electrochemical sensing of ascorbic acid (AA) was performed at room temperature using different concentrations ranging from 20 to 600 µM in 0.1M PBS of pH 7. The phosphate buffer solution (PBS, 0.1M, pH 7) served as a supporting electrolyte and was prepared using Na$_2$HPO$_4$ and NaH$_2$PO$_4$. Pure double distilled water was used in all experiments. All chemical reagents are of analytical grade and used as-received without further purification.

Synthesis of vitamin C tablet solution: The sensing performance was further applied to detect AA in commercially available vitamin C supplement Redoxon effervescent tablet. A tablet contains 1000 mg AA was readily dissolved in 50 mL PBS. Afterwards, 50 µL from the resulting solution was subsequently injected in the electrochemical cell containing 20 mL PBS for amperometric measurement, equivalent to 284 µM AA of tablet containing solution.

Photocatalytic reduction experiments: The photocatalytic reduction of Cr(VI) to Cr(III) was evaluated using the as-formed nanocomposite samples under visible light irradiation. 1 g/L of photocatalyst was dispersed in 100 ml Cr(VI) solution (potassium dichromate K$_2$Cr$_2$O$_7$ in deionized water) with a concentration 30 mg/L=0.1 mM in the presence of 5 mM citric acid as a reducing agent. At the beginning, to reach the adsorption-desorption equilibrium, the prepared suspensions were magnetically stirred for 30 min in the dark. Then, the suspensions were exposed to visible light irradiation (at $\lambda$>420 nm) produced by 250 W lamp (Osram, Germany). At regular time intervals, 2 ml of aqueous suspensions were withdrawn and the photocatalyst was removed by centrifugation. The remaining filtrate was analyzed by measuring the UV-vis spectra of Cr(VI) using UV-vis spectrophotometer.

Structural investigation of PSi, Sonicated PSi and AgNPs modified PSi nanocomposite: The XRD measurements of Si powder precursor, stain-etched PSi, sonicated (Son) PSi and AgNPs modified PSi are shown in FIG. 1. The presence of sharp peaks in all samples under investigation at Bragg angles of 28.50, 47.160, 56.10, 69.160, 76.50 and 88.00 corresponds respectively to (111), (220), (311), (400), (331) and (422) planes of Si phase (JCPDS no. 27-1402) (W. Ren et. al. (2016). However, in case of Ag/PSi sample beside Si phase peaks, appearance of four additional peaks at 2θ=38.170, 44.330, 64.30 and 77.50 can be very well indexed to (111), (200), (220) and (311) planes of face centered cubic phase (fcc) of silver respectively confirming the presence of Ag in newly formed modified structure. As also revealed, the obtained diffraction patterns of all XRD peaks are very sharp indicating the well crystalline nature of prepared samples.

Structural composition of all newly prepared samples has been further confirmed by FTIR spectroscopy. FIG. 2(A) shows the FTIR absorption bands obtained for Si, PSi, Son PSi and AgNPs modified PSi. As can be seen, in all samples a prominent peak appearing at around 625 cm$^{-1}$ is attributed to Si—Si stretching mode while the peaks appearing in the range of 1000-1300 cm$^{-1}$ correspond to the stretching mode of Si—O—Si groups. A small peak at 920 cm$^{-1}$ is attributed to Si—H$_2$ scissor mode. The presence of SiHx species in the outermost surface of PSi is confirmed by peaks appeared in the range of 2000-2300 cm$^{-1}$. A broad band appearing at 3440 cm$^{-1}$ and a small nudge at 1630 cm$^{-1}$ are due to deformation and asymmetrical stretching vibration mode of physically adsorbed H₂O molecules and structural hydroxyl group of SiOH, respectively. It has been observed that the presence of Ag in modified sample led to no major change except slight reduction in intensity or shifting of major peaks.

Raman spectroscopy has also been employed to further elucidate the structural composition. FIG. 2B depicts the Raman spectra of Si, PSi, Son PSi and AgNPs modified PSi. It has been observed that all samples showed a very well defined peak at around ~510 cm$^{-1}$ related to optical-phonon scattering at the center of the Brillouin zone of Si confirming the presence of nano-crystalline Si. A broad peak located at ~308 cm$^{-1}$ in all samples is associated with transverse acoustic (TA) vibrational mode. A slight red shift in band position from ~510 cm$^{-1}$ has been detected in case of PSi, Son PSi or AgNPs modified PSi and the band appeared at ~508 cm$^{-1}$; such a downshift of phonon frequency may be due to the developed tensile stress in the samples containing PSi due to their smaller lattice constant as compared to c-Si. As prepared samples of PSi have abundance of nanocrystalline silicon which could lead to the reduction in the lattice constant that in turn has resulting in downshift of phonon frequency. Additionally, a wide band appearing at 924 cm$^{-1}$ corresponds to the scattering of transverse optical phonons (F. A. Harraz et. al. (2016). It can also be seen that the absence of band at 480 cm$^{-1}$ in all samples confirms the crystalline nature of PSi samples.

Figure 3A:
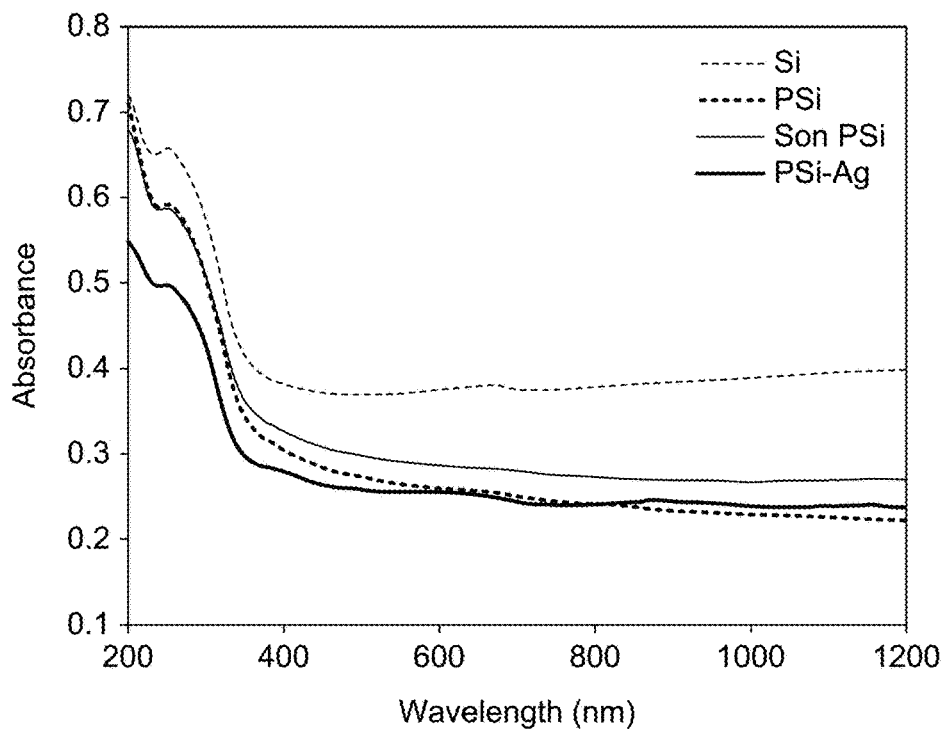
FIG. 3A. UV-vis absorbance spectra and FIG. 3B photoluminescence spectra of Si microparticles, stain-etched PSi, sonicated PSi and AgNPs modified PSi nanocomposite.
Figure 3B:
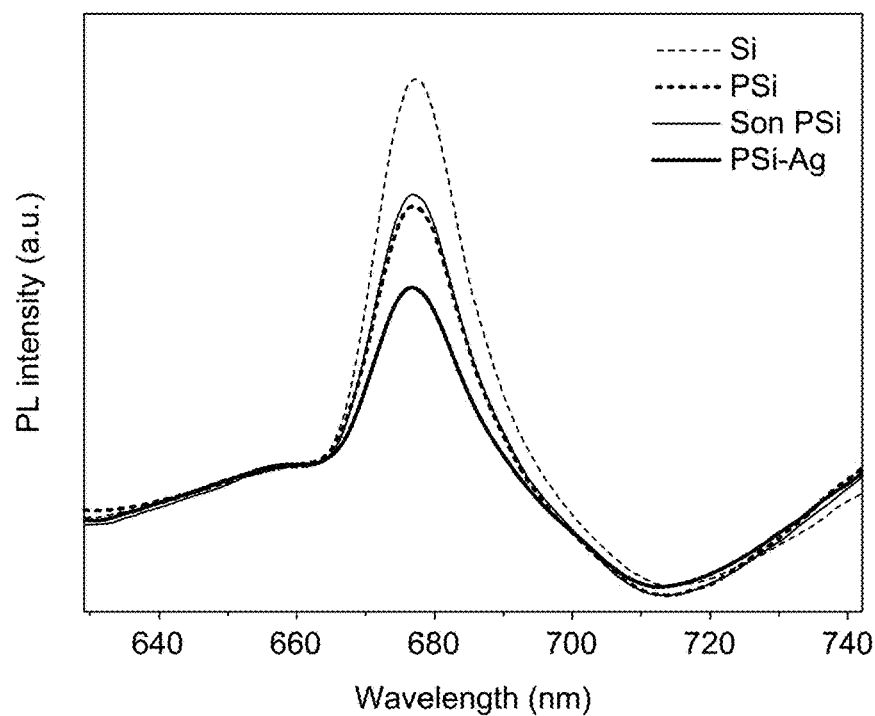

To examine the optical absorption characteristics of the synthesized materials, the UV-vis absorption spectra were measured in suspended aqueous solutions as shown in FIG. 3A. As a general trend, the spectral data revealed absorbance response in the visible range for all samples. Compared to Si precursor, the PSi, Son PSi and Ag modified PSi samples showed an increase in the cut off wavelength; i.e red-shifted, which indicates a narrowing in the band gap energy after porosification and/or Ag deposition. The narrowing in band gap has been typically observed in noble metal doped semiconductors, and can be attributed to the Surface Plasmon Resonance effect that often leads to a decrease of the effective band gap energy of the hybrid nanomaterial. This would help better and efficient absorbance of visible light during the photocatalysis experiments. The PL emission spectra of Si, PSi, Son PSi and AgNPs modified PSi are displayed in FIG. 3B. As could be observed, AgNPs modified PSi sample exhibited the lowest PL emission spectrum, which is a direct evidence for a much lower recombination rate of the photo-generated electrons and holes (A. Helal et. al. 2017). An efficient separation of the photo-generated charge carriers would play a major role in enhancing the photocatalytic reaction process.

Figure 4A:
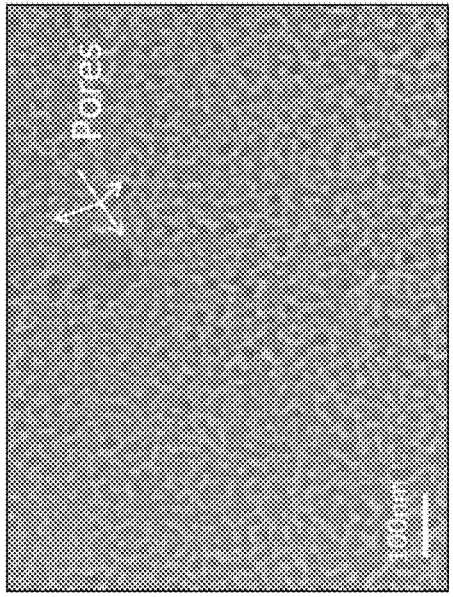
FIG. 4A. FESEM images of initial Si microparticles, FIG. 4B stain-etched PSi, FIG. 4C sonicated PSi and FIG. 4D AgNPs modified PSi nanocomposite.
Figure 4B:
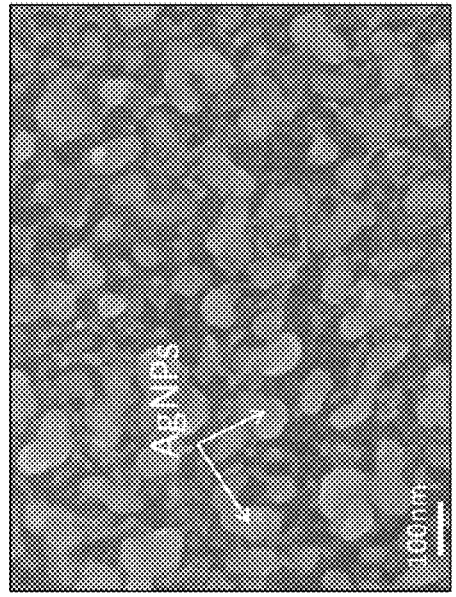
Figure 4C:
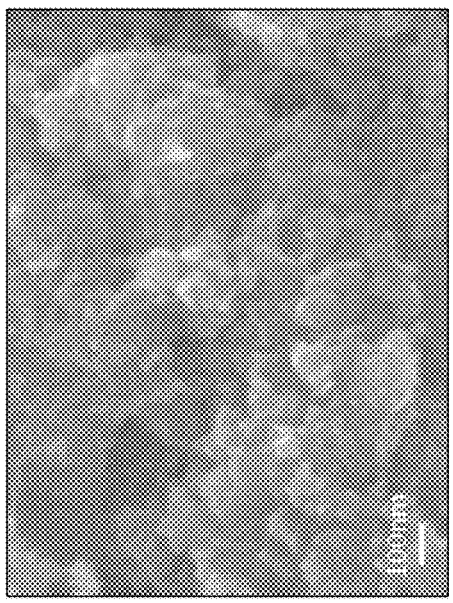
Figure 4D:
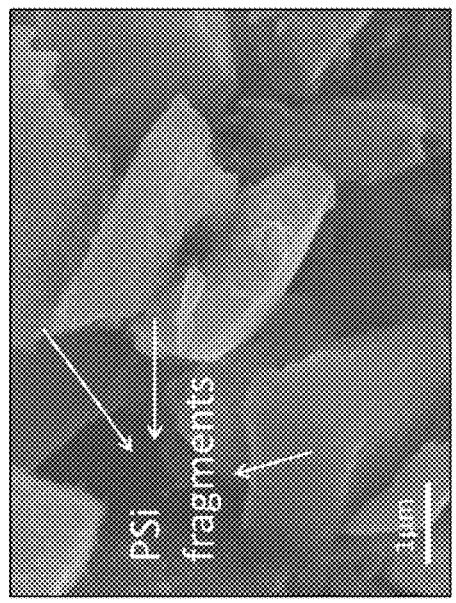

Surface morphology and structural examination have been carried out on Field emission-secondary electron microscope (FE-SEM). FESEM images of Si precursor, PSi, Son PSi and AgNPs modified PSi samples are shown in FIG. 4 (A, B, C, D). As revealed, the image of Si starting material, FIG. 4A, exhibits agglomerated spherical like particles morphology grown in high density. These agglomerated particles have stacking appearance giving sheet like morphology. The formation of porous structure is confirmed by the FESEM image of FIG. 4B. PSi has randomly distributed, high density pores with sizes <20 nm. For Son PSi sample, the sonication conducted on PSi led to a structure breakdown and formation of PSi fragments could easily be recognized in FIG. 4C image. In case of Ag modified PSi sample as shown in FIG. 4D, Ag nanoparticles are homogeneously anchored on PSi surface. This type of linkage between metallic Ag as a noble metal and PSi is very crucial in order to expedite the electron transfer mechanism in PSi which could be vital for the photocatalytic reaction event.

Figure 5A:
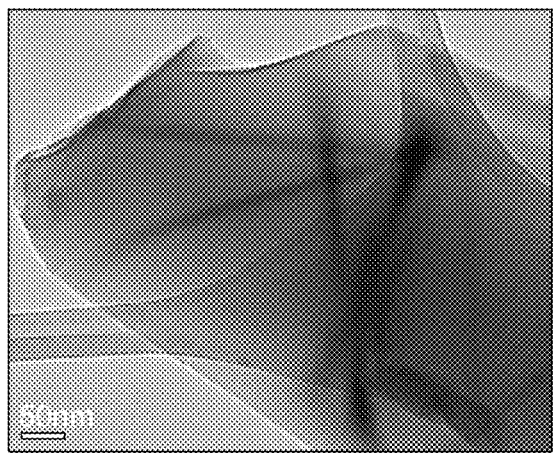
FIG. 5A. TEM images of initial Si, FIG. 5C PSi and FIG. 5E AgNPs modified PSi nanocomposite. The corresponding HR-TEM images are respectively shown in FIG. 5B, FIG. 5D and FIG. 5F. The SAED image of AgNPs modified PSi nanocomposite is shown as an inset FIG. 5G. Energy-Dispersive X-ray (EDX) analysis of AgNPs modified PSi nanocomposite is depicted in FIG. 5H.
Figure 5B:
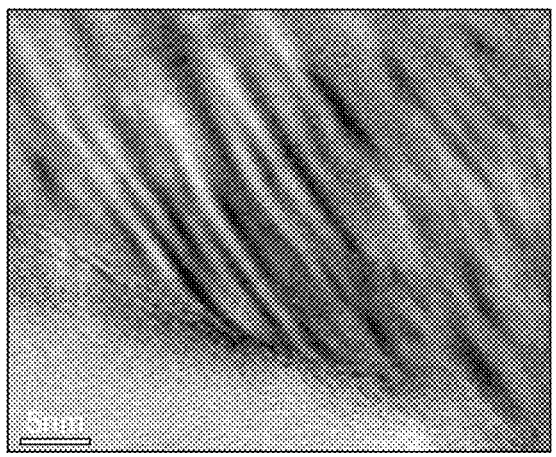
Figure 5C:
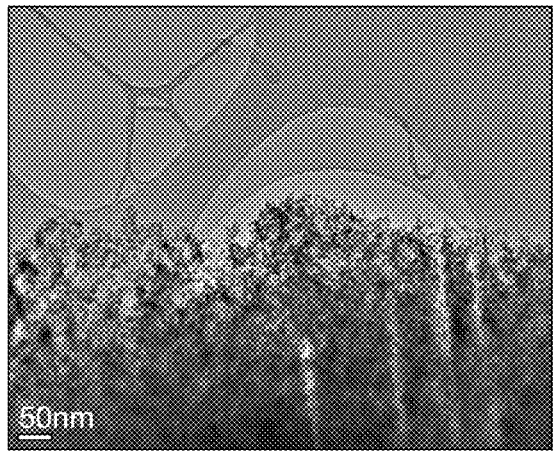
Figure 5D:
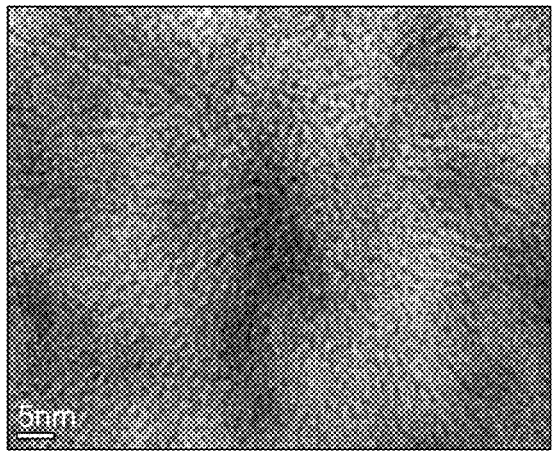
Figure 5E:
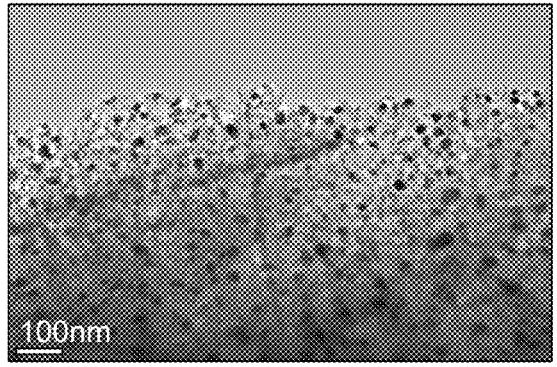
Figure 5F:
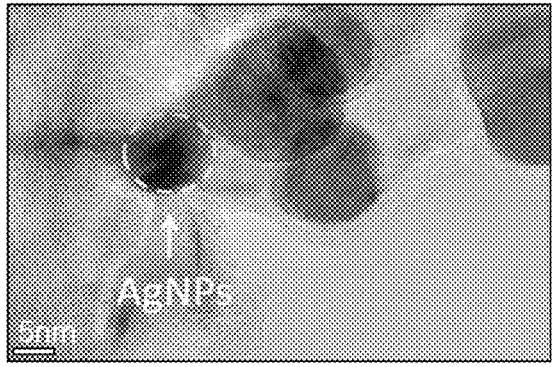
Figure 5G:
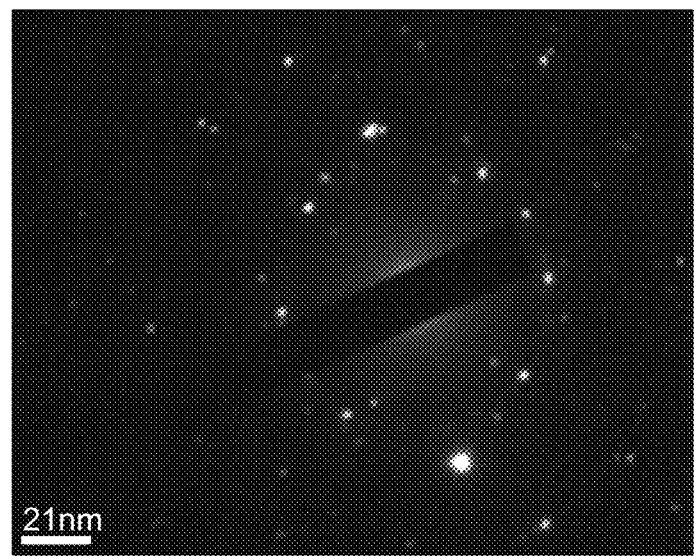
Figure 5H:
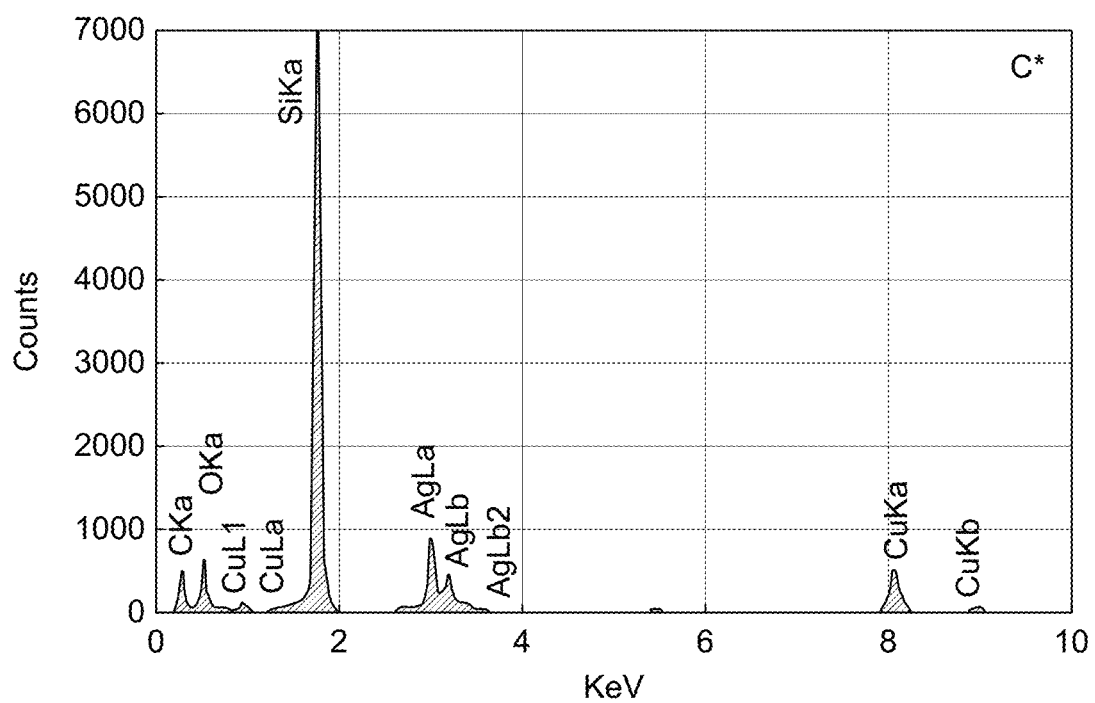

The structural morphology of synthesized samples Si precursor, PSi and Ag modified PSi was further observed by TEM as presented in FIG. 5A-H. It can be seen that starting silicon precursor shows sheet like structure which is transparent indicating that its thickness is in terms of few nanometers as in FIG. 5A. After imparting the porosity to the Si through stain etching process, tiny and random pores can be observed within the surface with sizes <20 nm corresponding to mesoporous regime as shown in FIG. 5C. Upon immersion plating of Ag nanoparticles, the PSi surface can be seen homogenously covered with spherical Ag nanoparticles with sizes ranging from 15-50 nm, FIG. 5E. High resolution TEM allows to have more deep sight into the samples as revealed from FIGS. 5(B, D and F). Si sheets show continuous crystalline matrix at higher magnification as in the FIG. 5(B). PSi shows the existence of crystalline nanoparticles surrounding small nanopores formed within its matrix FIG. 5(D). After performing Ag deposition, coexistence of crystalline Ag nanoparticles can be noticed along with crystalline Si nanoparticle and nanopores of the porous matrix FIG. 5(E). Selected area diffraction (SAED) measurement was conducted for Ag modified PSi sample as shown in the inset as image (FIG. 5G) It is clear that the sample shows spotty rings (FIG. 5 G) which mainly due to poly-crystalline character of Ag nanoparticles. In order to further confirm the purity and doping nature of the modified PSi sample, Energy Dispersive X-ray (EDX) measurement was carried out and shown in FIG. 5(H). The spectrum shows main Si peak characteristic for silicon together with carbon and copper peaks originating from the copper grid used for TEM observation. Furthermore, three peaks characteristic for Ag can be observed with Si peak which confirm the completion of Ag plating process. No other peaks were observed indicating the purity of the sample.

Figure 6A:
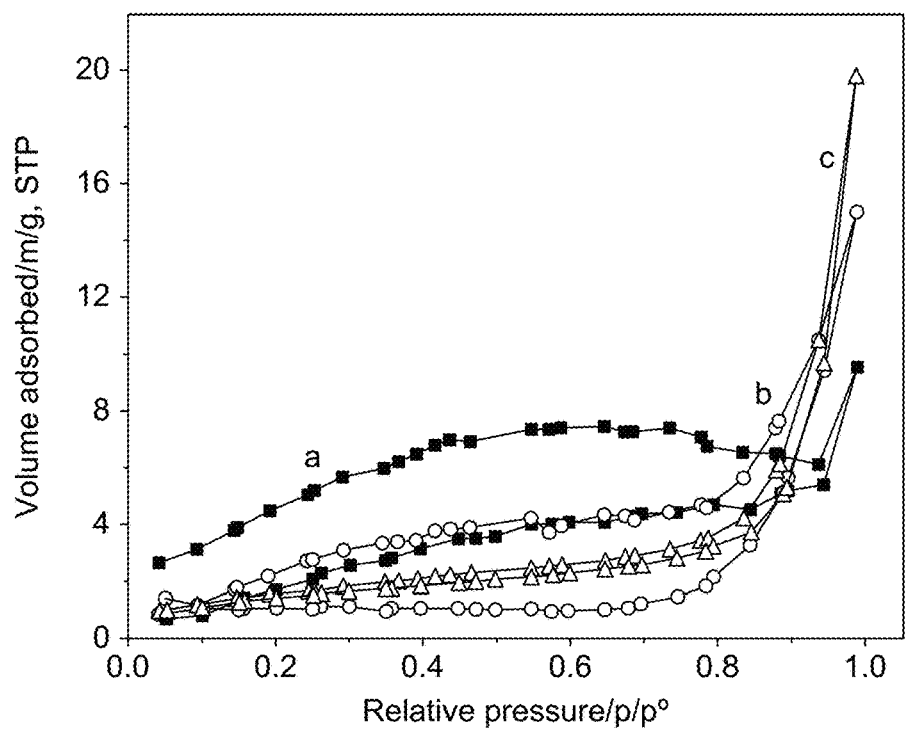
FIG. 6A $N_2$ sorption isotherms and FIG. 6B pore size distribution of (a) initial Si microparticles, (b) stain-etched PSi and (c) AgNPs modified PSi nanocomposite.
Figure 6B:
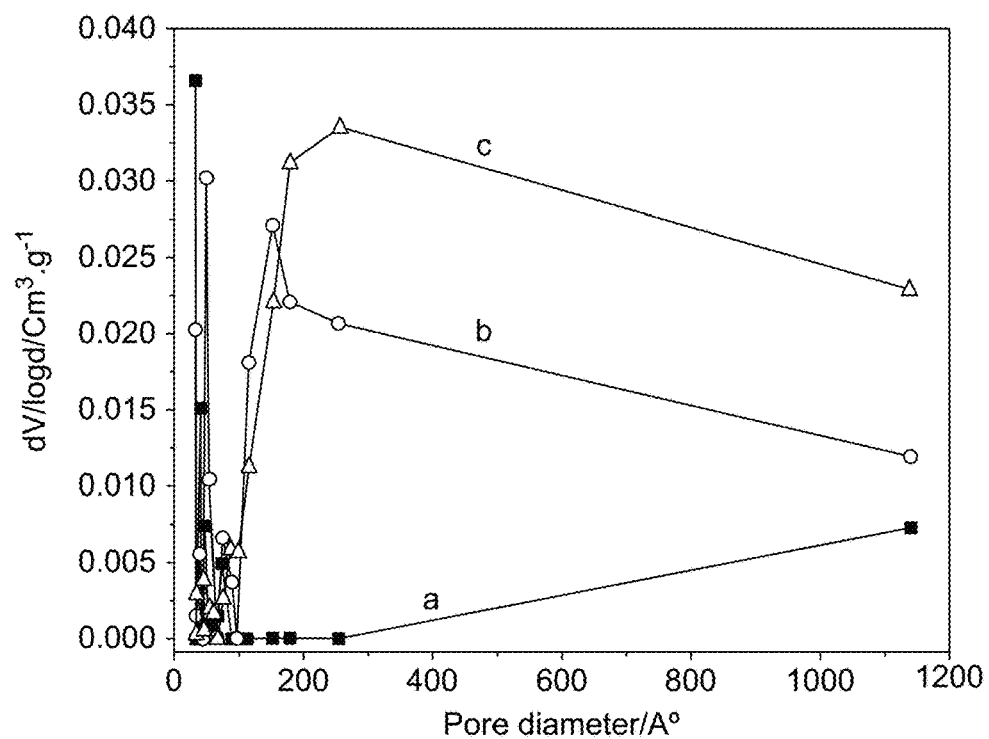

To evaluate the textural properties (specific surface area and total pore volume) of the Si precursor, PSi nanopowder as well as the AgNPs modified PSi, N₂ adsorption-desorption isotherm was conducted at 77 K and presented in FIGS. 6A and 6B. It is clear that both PSi and AgNPs modified PSi samples possessed type IV isotherm which is referring to porous materials, FIG. 6(A). The specific surface area and total pore volume for starting Si were 13.59 m²/g and 1.47×10$^{-2}$ cc/g, respectively, which indicates their low textural properties. Upon performing the stain etching process the surface area and total pore volume were significantly changed to 3.11 m²/g and 2.31×10$^{-2}$ cc/g, respectively where the surface area was deteriorated while the pore volume was boosted. However, increment of the pore volume after performing stain etching is quite expected since it creates pores but the decrement of surface area can be due to the bigger pores formed during etching process. Additionally, after the Ag deposition, the specific surface area and total pore volume were found to be 4.98 m²/g and 3.04×10$^{-2}$ cc/g, respectively. It is clear that surface area was enhanced due to the formation of small size Ag nanoparticles (15-50 nm), while the improvement of the pore volume can be attributed to the pores enlargement affected by immersion plating method. Finally, the pore size distribution, FIG. 6(B), for Si showed tri-modal pore size distribution profile with pore sizes around 4, 7 and 8 nm (curve a). After stain etching process, bigger pores of size 18 nm were observed together with small ones at 4, 7 and 8 nm to create multi-model pore size profile (curve b). Performing Ag deposition has boosted the size of bigger pores to reach 22 nm as well as their amount as seen in the curve c of FIG. 6(B).

Figure 7A:
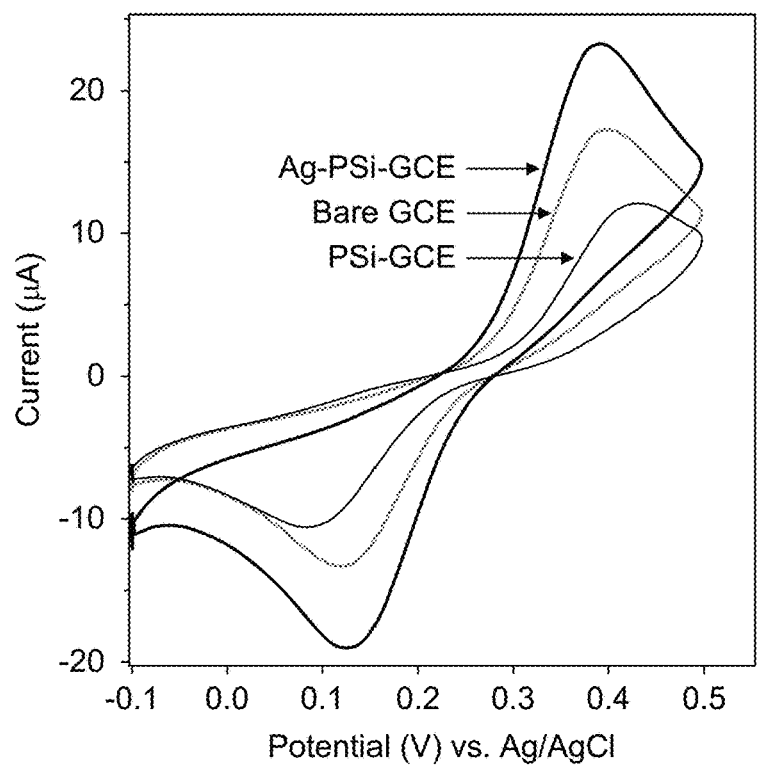
FIG. 7A Cyclic voltammetry (CVs) measured at 100 mV/s in 5 mM potassium hexacyanoferrate (1:1) [Fe(CN)$_6$]$^{3-/4-}$ and 50 mM KCl.
Figure 7B:
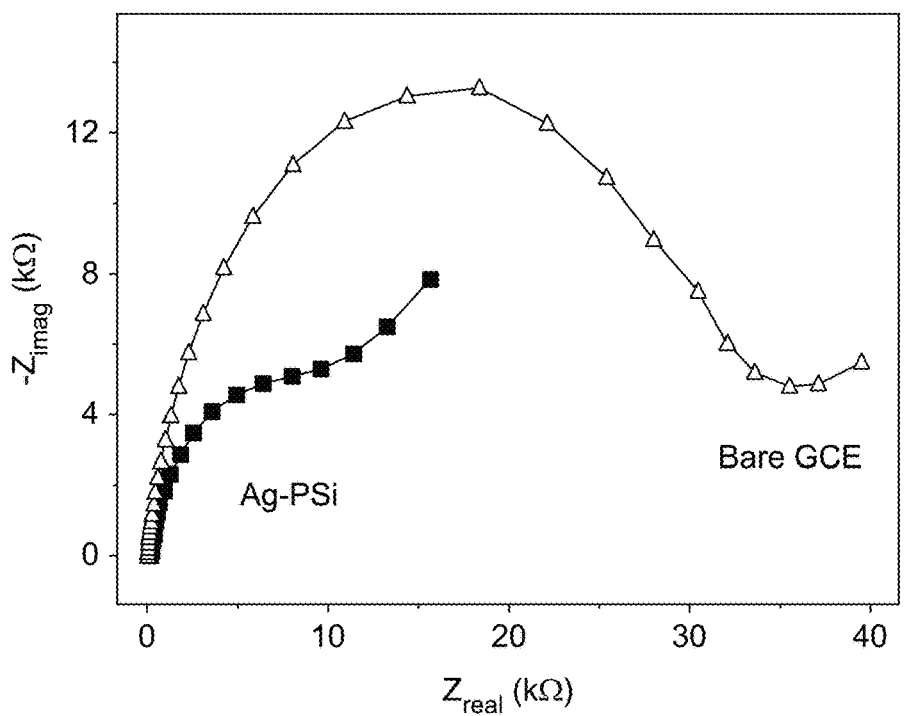
FIG. 7B Electrochemical impedance spectroscopy (EIS) Nyquist plots recorded at 0.3V; 10 mV amplitude and 10$^{-1}$ to 10$^5$ Hz.

Electrochemical sensing toward ascorbic acid: FIG. 7(A) compares CVs measured in standard redox probe of ferro/ferricyanide. As revealed, bare GCE itself exhibits appreciable electron transfer, whereas a reduction in redox process was detected at PSi-GCE. Meanwhile, a large, well-defined redox response was obtained at Ag—PSi/GCE, indicating a significant enhancement in electron transfer rate (~140% of bare GCE). Enhancement of electron transfer at Ag—PSi modified GCE was also obvious from EIS Nyquist plots, FIG. 7(B). The response of GCE indicated the electrode kinetics is dominantly under electron transfer at almost all frequencies. However, Ag—PSi showed smaller charge transfer resistance, with a linear part suggesting a diffusion control at the intermediate frequency values. The outstanding electrocatalytic properties of AgNPs-PSi/GCE may be attributed to mesoporous structure of PSi, along with high density and nanoscale range of catalytic Ag particles. An enhancement response during the electrochemical determination of hydrogen peroxide using a similar nanocomposite modified carbon paste electrode has been recently reported.

Figure 7C:
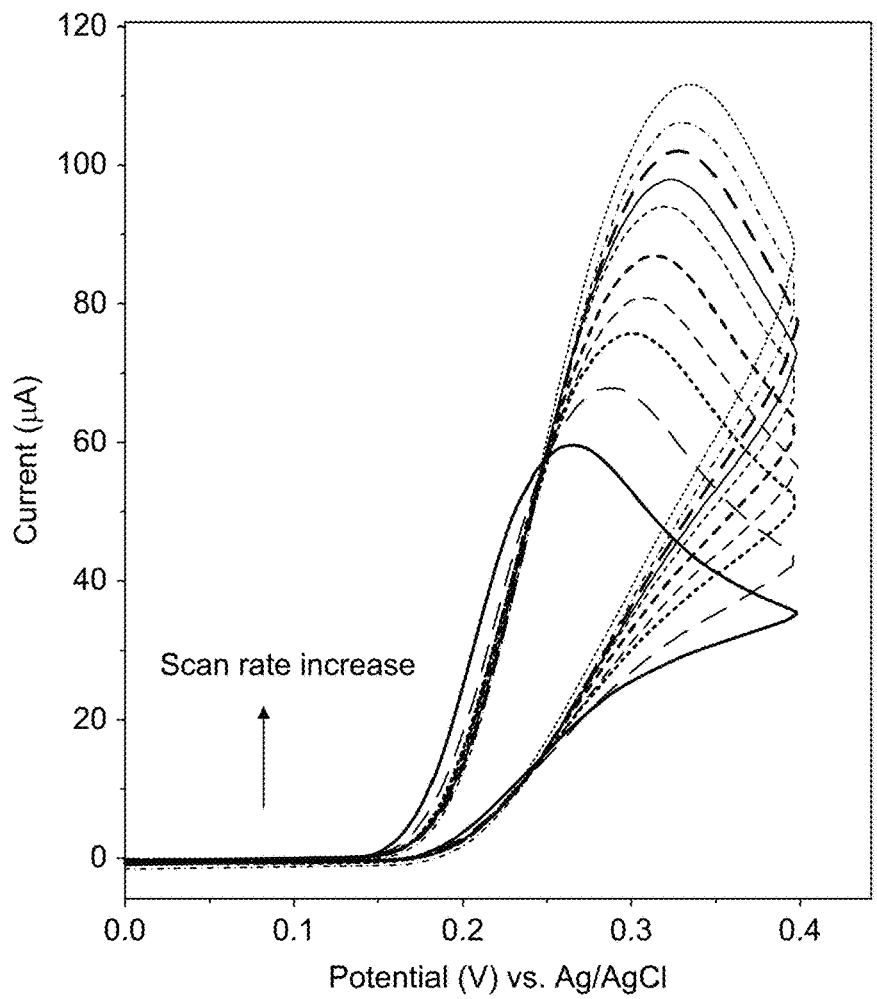
FIG. 7C CVs at different scan rates (10-100 mV/s) in 0.1M PBS in presence of 1 mM AA using PSi—Ag/GCE.
Figure 7D:
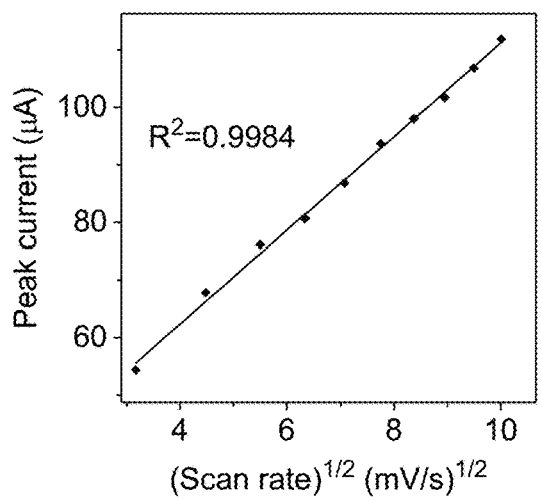
FIG. 7D Peak current vs. square root of scan rate and FIG. 7E Peak potential vs. Ln scan rate.
Figure 7E:
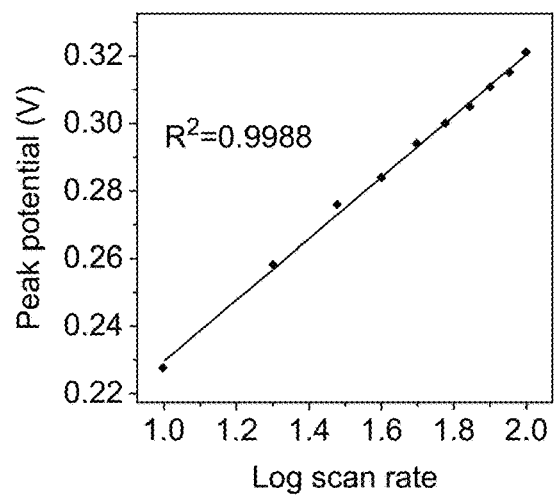

FIG. 7(C) shows CVs measured at various scan rates, where well-defined oxidation peaks of AA increase in intensity as the scan rate increases, with a slightly potential shift to positive direction. FIG. 7(D) presents a good linear relation between oxidation peak current ($i_{pa}$) and square root of scan rate with a regression equation: $i_{pa}$ (µA)=30.278 v½ (mVs$^{-1}$)½+8.1198 with R$^2$=0.9984, indicating a diffusion-controlled process, which is advantageous for amperometric sensing. Linear plot was also obtained for oxidation peak potential versus logarithm of scan rate, FIG. 7(E), with a regression equation: $E_{pa}$ (V)=0.1396 log(v)+0.0903 with R$^2$=0.9988. The electrocatalytic oxidation event proceeds accordingly via a two-electron, two-proton pathway leading to the formation of dehydroascorbic acid. A comparison with other AA sensors based on Ag nanostructures is collected in table 1, showing outstanding sensing performance of the electrode developed in this work.

Table 1 Comparison of electrode performance with other modified electrodes based on Ag nano structures.

| Modified electrode | LOD (µM) | Sensitivity (µAµM$^{-1}$) | Linear range (µM) | Ref. |
|---|---|---|---|---|
| AgNPs-rGO | 9.6 | 0.45 | 10-800 | Kaura et. al. 2013 |
| AgNPs | 0.1 | 0.0639 | 0.4-450 | M.A. Khalizadeh et. al. 2016 |
| AgNPs-P(Arg)-GO | 0.984 | 0.03 | 4-2400 | G.A. Tig, 2017 |
| Ag hierarchical structure | 0.06 | 0.0355 (µAµM$^{-1}$cm$^{-2}$) | 0.17-1800 | Y. Zhnag et. al. 2018 |
| Ag hexacyanoferrate NPs | 0.42 | — | 4-78 | M. Noroozifar et. al. 2010 |
| AgNPs/PSi | 0.83 | 1.279 (µAµM$^{-1}$cm$^{-2}$) | 20-600 | Instant claimed invention |

Figure 8A:
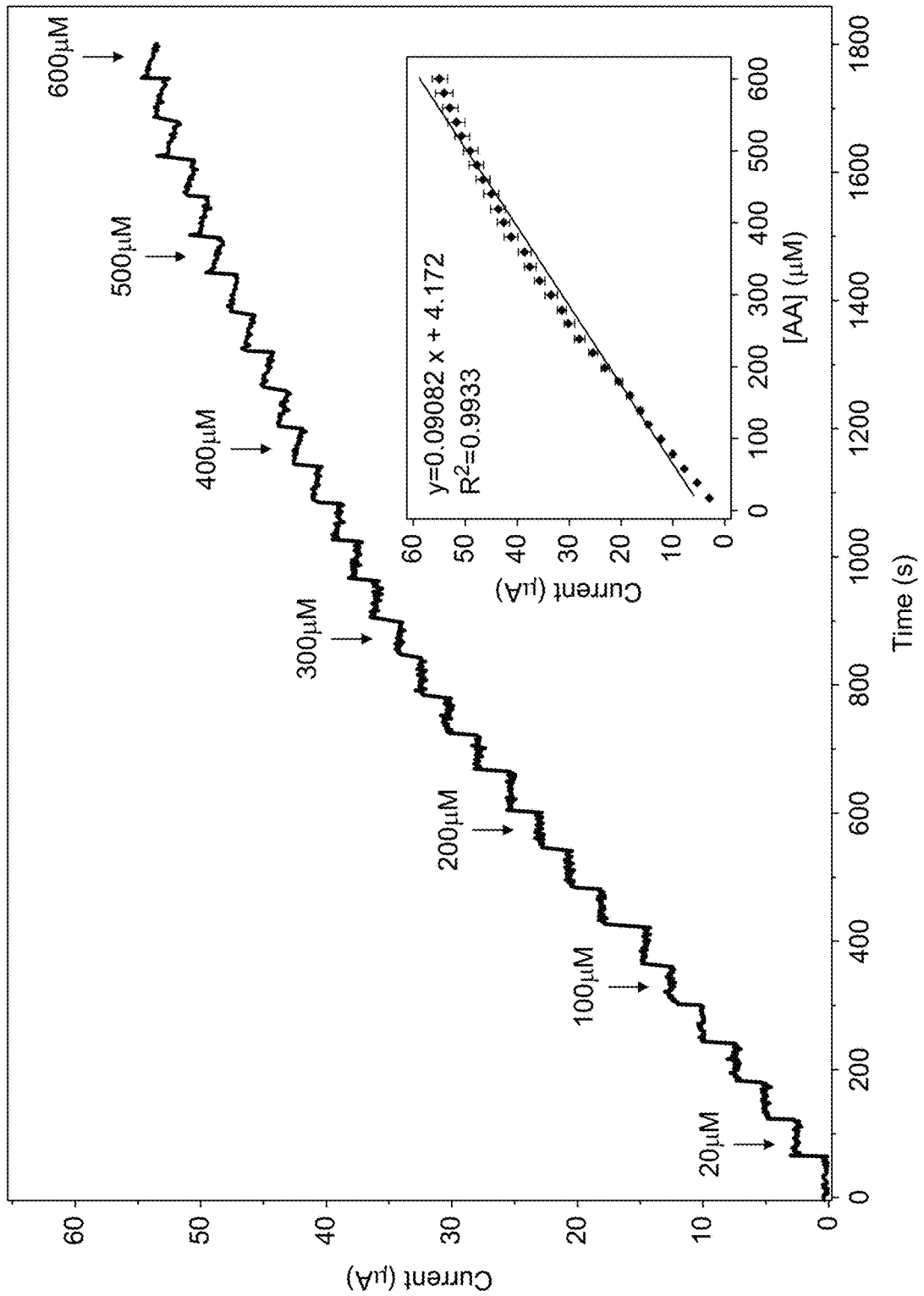
FIG. 8A Amperometric response of PSi—Ag/GCE to successive additions of AA (20 to 600 µM) into stirred 0.1M PBS at 0.3V, inset shows calibration curve.

The amperometric response with a staircase curve was obtained upon successive injections of AA, FIG. 8(A). A steady state current was rapidly achieved within response time <5 s, indicating sensitive detection of AA at the AgNPs-PSi/GCE surface. The calibration plot between peak current and AA concentration gives straight line shown in inset (R$^2$=0.9933) for a wide concentration range (20-600 µM), giving by the fitting equation (5):

$$I (µA)=0.09082 [AA] (µM)+4.172 \qquad \text{Equation 5}$$

The sensor sensitivity was calculated as the slope line per electrode area (0.071 cm$^2$) and equals 1.279 µAµM$^{-1}$cm$^{-2}$. The limit of detection (LOD) based on a signal-to-noise ratio (S/N=3) was estimated as 0.83 µM.

Figure 8B:
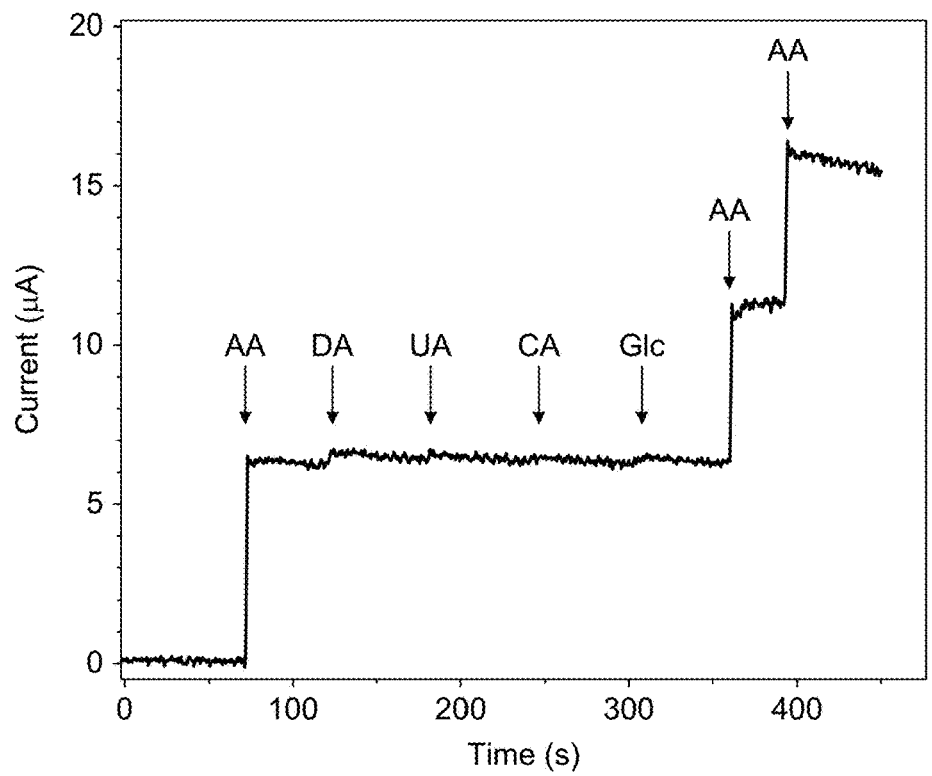
(FIG. 8B) Interference behavior for 50 µM AA (beginning) or 40 µM at last two injections with successive additions of 100 µM of DA (dopamine), UA (uric acid), CA (citric acid), or Glc (glucose).

Selectivity test was conducted in presence of common active species, FIG. 8(B); where excellent anti-interference behavior was notably recognized. Good reproducibility was achieved using three different electrodes, giving a relative standard deviation (RSD) ~2.9%. A repeatability test for ten successive runes in 50 µM AA led to RSD ~3.5%. A minimal reduction in sensitivity was detected after three weeks electrode storage in ambient conditions, which are all beneficial for practical use.

Figure 8C:
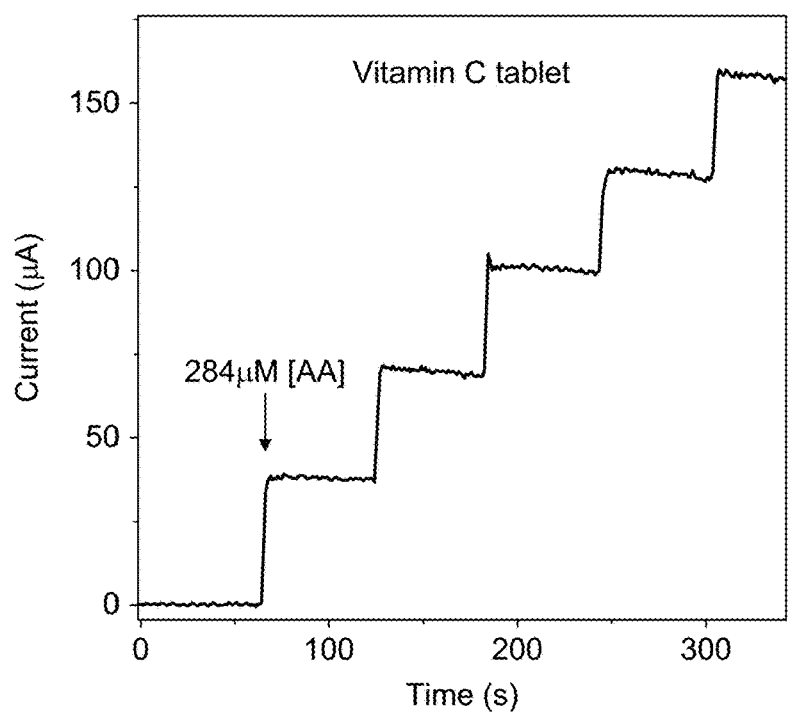
(FIG. 8C) Amperometric response recorded upon 5 injections containing each 284 µM Redoxon vitamin C.
Figure 9A:
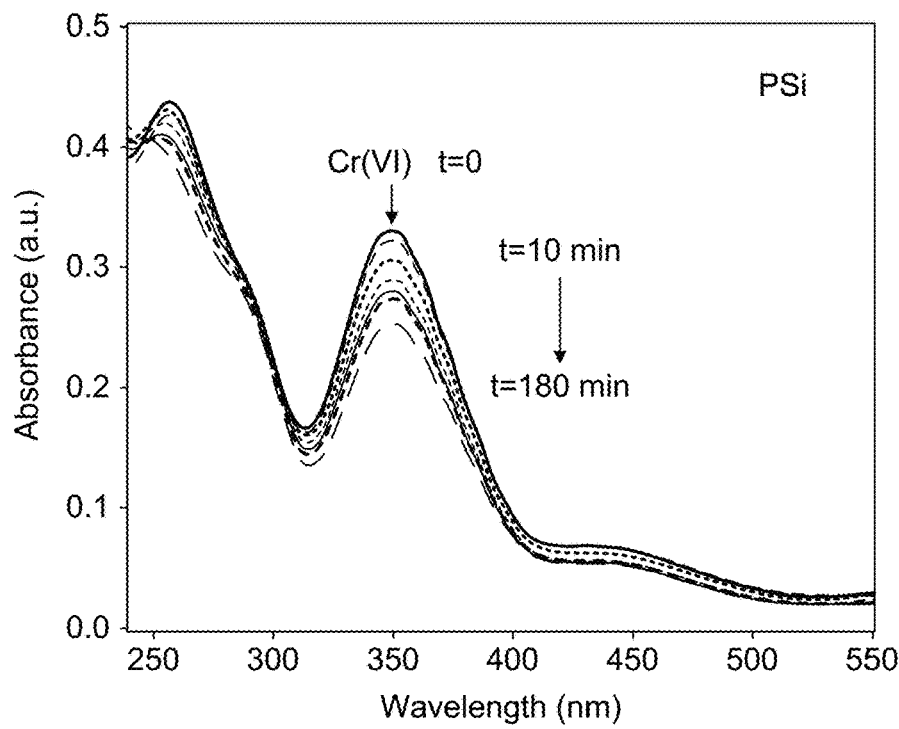
Figure 9B:
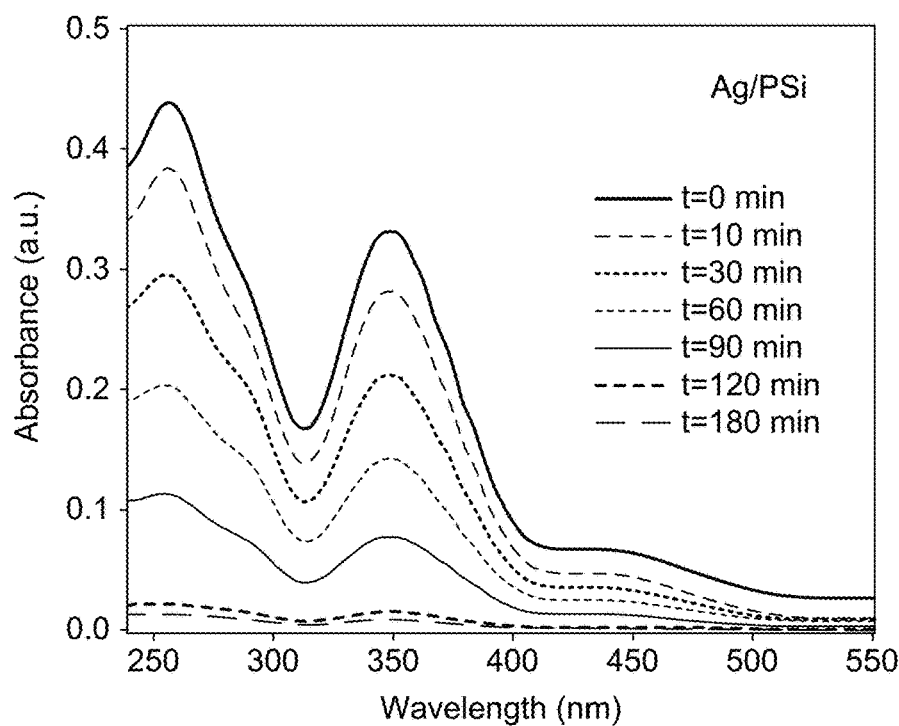
Figure 9C:
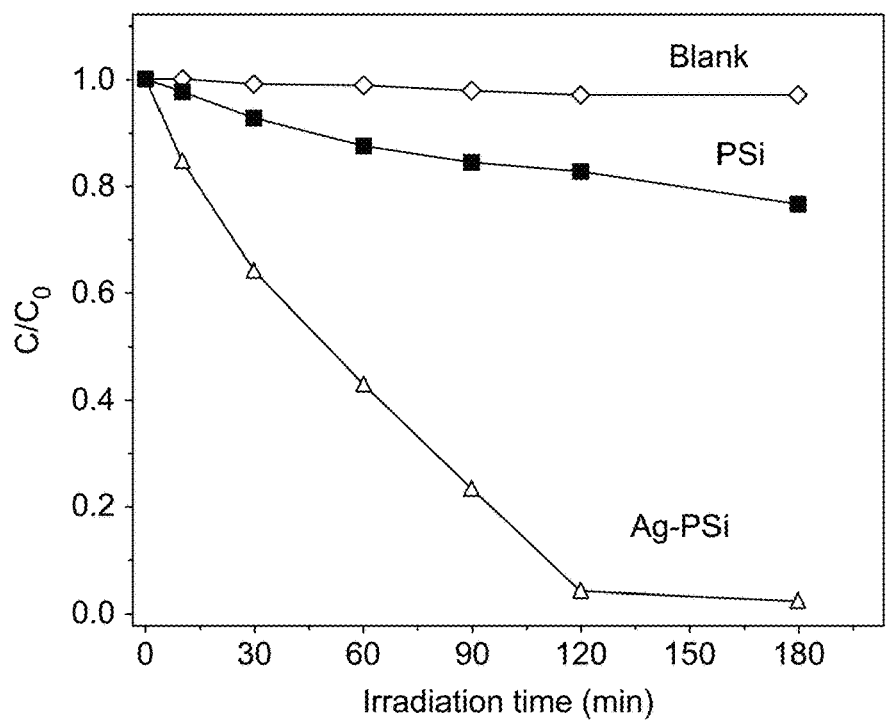
Figure 9D:
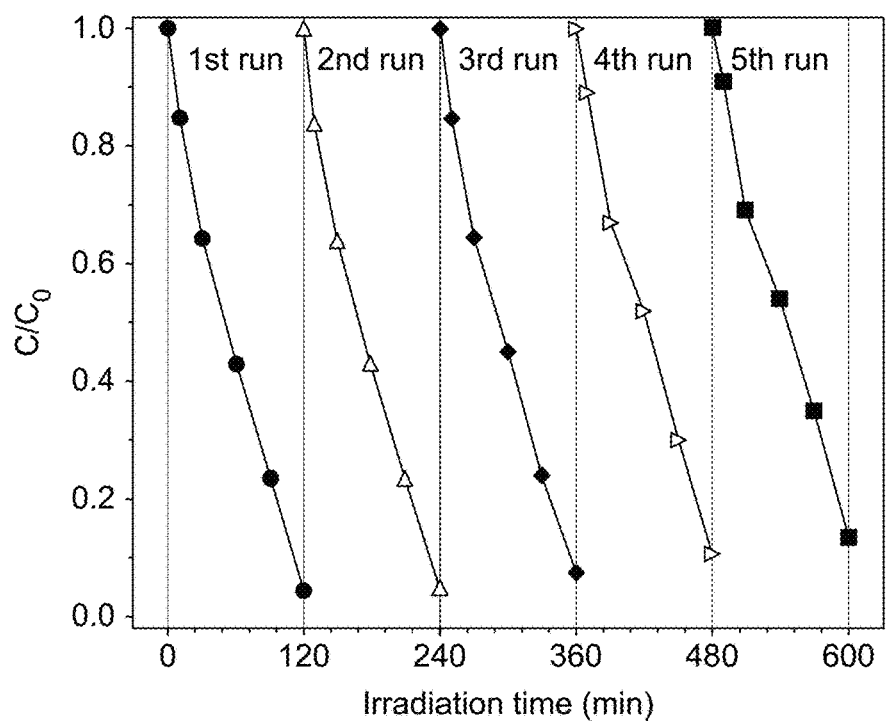

FIG. 8(C) shows five sequential injections from vitamin C tablet solution, each injection is equivalent to 284 µM AA. This gives an average amperometric current 32.0 µA, which, from Eq. (1) corresponds to AA concentration 306 µM. This measured concentration value represents ~108% of original concentration which is in close agreement with the tablet description.

Photocatalytic reduction of Cr(VI): The photocatalytic reduction of aqueous Cr(VI) solution using the newly synthesized photocatalysts was performed at room temperature with the assist of visible light irradiation. The change in Cr(VI) spectral absorption profile with time is taken as the indicating property for the reduction event. The Cr(VI) solution displays a couple of absorption bands, notably at ~256 and 350 nm (FIG. 9). The photo-reduction process was consequently monitored by the decay of the 350 nm absorption band. Firstly, no reduction reaction was observed under dark condition for 30 min in the presence of active AgNPs modified PSi catalyst. Secondly, the blank test, i.e. the direct irradiation of Cr(VI) solution under visible light in absence of phtotocatalyst led to a negligible reduction percentage <5% after 180 min. That means the Cr(VI) solution is apparently stable either in the dark even in the presence of the photocatalyst or under irradiation in absence of photocatalyst.

The photocatalytic reduction of Cr(VI) in the presence of Si precursor microparticles, stain-etched PSi, Son PSi or AgNPs modified PSi in the presence of 5 mM citric acid under visible light irradiation was smoothly investigated. Si microparticles led to a decline in initial absorption intensity by only ~10% after 180 min irradiation treatment. Under identical experimental conditions, 23% reduction efficiency was observed using the PSi sample, see spectra change using PSi, FIG. 9(A), and the normalized temporal changes of concentration (C/C$_0$) of FIG. 9(C). In case of Son PSi and due to the breakdown of porous structure only 12% reduction efficiency was achieved after 180 min reaction. This result indicated that either Si microparticles, PSi alone or Son PSi are considered inactive photocatalysts for Cr(VI) reduction under visible light. A possible reason for such low absorption intensity decrease is due to the adsorption tendency of Cr(VI) ions on photocatalyst surfaces rather than from the photo-reduction process. However, significant enhancement of the photocatalytic reduction of Cr(VI) was obviously detected using the AgNPs modified PSi photocatalyst under the identical experimental conditions. The UV-vis absorbance profile of Cr(VI) decreased rapidly with time reaching a value <5% of the initial band intensity after 120 min treatment, FIG. 9(B). In temporal concentration changes of FIG. 9(C), one could notice that ~57% reduction efficiency was achieved after 60 min irradiation, increased rapidly to ~76% after 90 min, whereas an efficiency of 95.5% was observed after 120 min, and by increasing the irradiation time to 180 min a further small increase of the efficiency to a maximum value of 97.4% was achieved.

The photo-stability of as-synthesized AgNPs modified PSi nanocomposite photocatalyst was evaluated through five consecutive experimental runs of the photo-reduction of Cr(VI) in the presence of 5 mM citric acid, FIG. 9 (D). For the next use, the photocatalyst was firstly removed from the reaction medium via a simple filtration process, followed by washing using pure water and suitable drying. The photocatalytic degradation efficiency remains almost the same at a maximum value of 95.5% during the first two runs. The reduction efficiency slightly dropped in cycles three and four, yielding 92.4% and 89.3%, respectively. In the experimental run five, the photocatalyst exhibited 86.5% reduction efficiency. The slight deactivation of AgNPs modified PSi photocatalyst seems to be related to the adsorption of Cr(III) product onto the catalyst surface. Another possibility for such a deactivation behavior is likely due to a catalyst leaching or weight loss as the result of repeated filtration steps.

It is commonly accepted that the photocatalytic performance is notably dependent on the adsorption capability of catalyst along with its surface catalytic behavior, extent of light utilization and the efficient separation of photo-generated electrons and holes. Particularly, the poor separation of the photo-generated charge carriers corresponding to fast recombination rate between electrons and holes is considered a severe drawback that greatly limits the proper working of the photocatalyst. In the present work, the Si hydrides formed on the surface of PSi after stain etching and confirmed by the above FTIR measurement could serve as a trapping moiety for electrons, leading to enhance the separation between electrons and holes, which resulted in promoting the photocatalytic activity. However, the enhancement in photocatalytic activity using PSi alone as a photocatalyst was small. Significant enhancement of the photocatalytic performance was achieved using AgNPs modified PSi photocatalyst. It has been reported earlier that coating the Si nanostructures by noble metal nanoparticles or even by less noble metal such as Cu could increase the photocatalytic activity during the decontamination of aqueous organics. Similarly, in the present work, the AgNPs decorated the surface of stain-etched PSi increased the separation rate between electrons and holes enabling better utilization of light and lowering the recombination rate as evidenced experimentally by the PL spectra of FIG. 3B.

A possible reaction mechanism for the photo-reduction of Cr(VI) onto the AgNP modified PSi photocatalyst under visible light irradiation would be expressed as the following equations:

Table 2: Equations:

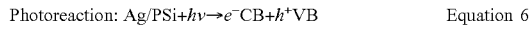

Photoreaction: Ag/PSi+$h\nu \to e^-$CB+$h^+$VB     Equation 6

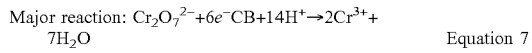

Major reaction: $Cr_2O_7^{2-}$+$6e^-$CB+$14H^+ \to 2Cr^{3+}$+ $7H_2O$     Equation 7

$H_2O$+$h^+$VB$\to$OH.+H+     Equation 8

$Cr^{3+}$+$2h^+$VB+OH.$\to Cr^{6+}$+$OH^-$     Equation 9

A photoreaction takes place according to Equation 6 upon the direct irradiation of the Ag/PSi catalyst in a way that an $e^-$-$h^+$ pairs are photo-generated. The presence of AgNPs decorating the PSi surface would serve as $e^-$ trapping to help a proper separation between $e^-$ and $h^+$ and hence the electrons are readily captured by Cr(VI), leading to the formation of the reduced form Cr(III), Equation 7. The catalyst under photoexcitation would react with $H_2O$ molecules leading to the formation of OH. radicals, Equation 8. A possible back reaction of Cr(III) with the oxidative $h^+$ and OH. radicals could lead to the formation of Cr(VI), Equation 9. The presence of citric acid (CA) as an organic compound promotes the photoreduction reaction of Cr(VI) to Cr(III) via dual functions; (i) CA acts as a hole scavenger, minimizing the re-oxidation back reaction of Cr(III) to Cr(VI) as shown in Equation 9, and (ii) suppresses the rate of $e^-$-$h^+$ recombination through rapidly consumption of photo-generated holes. That means the oxidation of CA under photoexcitation is considered as a sacrificial reaction of the unfavorable re-oxidation reaction of Equation 9. Photocatalytic experiment conducted in absence of CA showed significant decline of the photo-reduction efficiency of Cr(VI) to Cr(III). The initial CA concentration of 5 mM seems optimum value to enhance the photocatalytic reaction event, below such a concentration is insufficient for better separation of e and $h^+$, resulting in a decline in the photo-reduction process. The overall reaction in the current catalytic system is therefore the photo-reduction of Cr(VI) to Cr(III) and simultaneous oxidation of CA to $CO_2$, such a combined reaction can be expressed as the following Equation 10:

Equation Shown in Table 3:

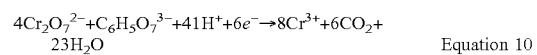

$4Cr_2O_7^{2-}$+$C_6H_5O_7^{3-}$+$41H^+$+$6e^- \to 8Cr^{3+}$+$6CO_2$+ $23H_2O$     Equation 10

Figure 10:
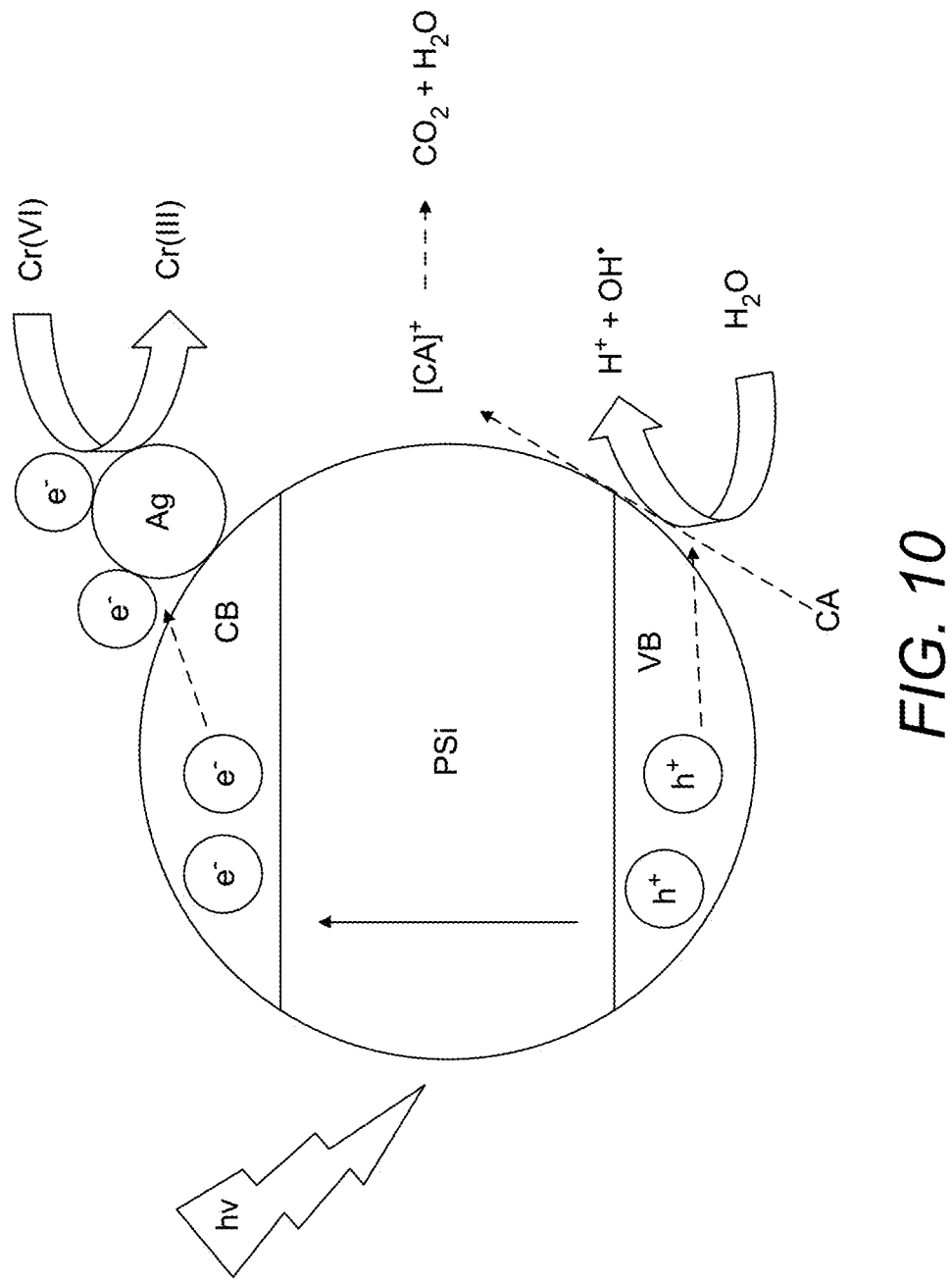
FIG. 10. An illustration shows the photocatalytic reduction mechanism of Cr(VI) over AgNPs/PSi nanocomposite. (VB: valence band; CB: conduction band; e$^-$: electrons; h$^+$: holes; CA: citric acid).

In an earlier work (O. Fellahi et. al. 2016), it has been reported that the addition of either adipic acid or citric acid led to a significant enhancement of Cr(VI) photoreduction at SiNWs photocatalyst, which is consistent with the current research findings. Furthermore, previous reports have demonstrated also that organic compounds could act as sacrificial electron donor and subsequently accelerated the photo-reduction rate of Cr(VI) using $TiO_2$-based photocatalysts. Based on the discussion above, the photocatalytic reduction mechanism is illustrated in FIG. 10.

In summary, an efficient ascorbic acid (AA) amperometric sensor based on novel AgNPs-PSi modified GCE has been developed using simple fabrication procedures. Highly sensitive, selective sensor performance, along with rapid response time, low LOD and electrode stability are major key features of current developed electrode. The electrode accuracy has been testified using a practical sample of vitamin C tablet, with reliable quantification results. Additionally, modification of such PSi surface by AgNPs was found to significantly enhance the photo-reduction reaction of Cr(VI) to Cr(III) in the presence of citric acid, with the assist of direct visible light illumination leading to a maximum removal efficiency of 97.4% after 180 min, compared to sluggish conversion rates of 10%, 12% or 23% using Si microparticles, sonicated PSi or unmodified PSi samples, respectively. The enhanced photocatalytic reduction of Cr(VI) to Cr(III) was notably related to the efficient separation of the photo-generated $e^-$-$h^+$ pairs as confirmed by the photoluminescence spectral measurement. Moreover, addition of citric acid to dichromate solution could promote the photo-reduction reaction as it essentially takes part in the oxidation reaction, which helps to minimize the unfavorable re-oxidation reaction of Cr(III) to Cr(VI). The current photocatalyst could be reused five times with a minimal loss in its photocatalytic activity. The obtained research findings here signified fundamental needs to further developing Si nanostructures doped with noble metal nanoparticles or conducting polymers and their utilization as either efficient chemical sensors or visible-light photocatalysts for environmental remediation.

What is claimed is:

1. A method of chemical sensing and quantifying of an ascorbic acid (AA) in a solution, comprising:
    forming an active paste by mixing weight % of 80% of a silver nanoparticle-mesoporous nanocomposite and 20% of a butyl carbitol acetate and ethyl acetate binder; wherein the mesoporous silicon is semiconductive;
    coating the active paste onto a surface of a glassy carbon electrode followed by drying at 65° C. for 6 hours until a dried glassy carbon electrode of a uniform surface is obtained, and chemical sensing and quantifying of the ascorbic acid (AA) in the solution using the said dried glassy carbon electrode having a coat of the active paste through an amperometric current transient response (current versus time).

2. The method of claim 1, wherein making the silver nanoparticle-PSi nanocomposite comprises:
    adding 10 mL of 48% hydrogen fluoride and 40 mL of water to 1 gram of silicon powder of specific diameter;
    adding dropwise 2.5 mL of 70% $HNO_3$ under continuous stirring at room temperature;
    stain etching for 15 minutes after observing emitted nitrogen oxide to make the PSi; and
    filtering and washing the PSi with a water and drying it at room temperature to obtain a dried PSi.

3. The method of claim 2, wherein the making the silver nanoparticle-PSi nanocomposite further comprises:
    performing immersion plating by combining 0.5 grams of the dried PSi with 80 mL of 0.1M HF;
    adding 5 mL of 0.05M $AgNO_3$ dropwise by continuously stirring and collecting a non-dry silver nanoparticle-PSi nanocomposite; and
    filtering and drying the non-dry silver nanoparticle-PSi nanocomposite to obtain the silver nanoparticle-PSi nanocomposite.

4. The method of claim 3, wherein the silver nanoparticle-PSi nanocomposite is composed of the PSi with a pore size of less than 20 nm, decorated with crystalline silver nanoparticles of 15-50 nm size.

* * * * *